United States Patent [19]

Brown et al.

[11] Patent Number: 5,396,366
[45] Date of Patent: Mar. 7, 1995

[54] ENDOSCOPE APPARATUS

[75] Inventors: Frank J. Brown, Willow Grove; Eric F. Brown, Chalfont, both of Pa.

[73] Assignee: Sigma Dynamics Corporation, Willow Grove, Pa.

[21] Appl. No.: 26,534

[22] Filed: Mar. 4, 1993

[51] Int. Cl.⁶ ............................................. A61B 1/00
[52] U.S. Cl. .................................. 359/435; 359/652; 359/819; 128/4; 128/6
[58] Field of Search ............... 128/6, 4; 359/819, 435, 359/652

[56]  References Cited
U.S. PATENT DOCUMENTS 4,515,444  5/1985  Prescott et al. ................... 359/654
5,188,092  2/1993  White ............................ 359/435 X

*Primary Examiner*—Do Hyun Yoo
*Attorney, Agent, or Firm*—John W. Logan, Jr.

[57] ABSTRACT

An endoscope is disclosed which is designed to transmit light to the area under observation and allows the light to make contact with the image plane, without the need of a fiber optic bundle. The ocular section of the endoscope, in addition to housing the lenses required to magnify the image for viewing, contains a relay lens whose diameter is less than the diameter of the rod lenses in the relay section. Light is then reflected through a beam director surrounding the ocular relay lens and transmitted to the objective through the excess diameter of the larger diameter relay lenses. Additionally, the ocular section is separable from the relay and objective sections, which are considered disposable, so that it can be reused.

10 Claims, 2 Drawing Sheets

ENDOSCOPE APPARATUS

BACKGROUND OF THE INVENTION

1. Field of the Invention

The present invention relates to an endoscope for use in medical and other procedures. More particularly, the present invention provides an improved means of transmitting light from an ocular end to an objective end of the scope in order to illuminate the area under observation. The present invention also provides an improved light and image transmitting lens portion which can be a disposable item.

2. Description of Prior Art

Endoscopes are widely used today to assist in a variety of medical and other procedures. With the growing importance of the practice of minimally invasive surgery, the need for high quality and low cost endoscopes has grown substantially.

A typical endoscope is generally divided into three main sections: an objective section; a relay section; and an ocular section. The objective section is that portion of the endoscope that is inserted into the body. The relay section transmits the image from the objective section to the ocular section. The ocular section magnifies the image for viewing by an operator.

Basically, two types of endoscopes are employed for surgical medical procedures—flexible endoscopes and rigid endoscopes. The flexible endoscope uses an optical fiber bundle to relay the image from the objective section to the ocular section. The endoscope is flexible because of the ability of the fiber bundle to bend while still transmitting an image.

The rigid endoscope uses lenses instead of fibers to transmit the image. The main advantage of using lenses to relay the image is that lenses provide better resolution and brightness, the brightness being determined by the optical invariant of the relay section. Thus, rigid endoscopes are preferred for many medical procedures where image quality is crucial.

The use of radial gradient-index rod lenses, usually referred to as "GRIN" lenses, in endoscopes is well known. These lenses are commercially available from the Nippon Sheet Glass Co., Ltd. and its U.S. affiliate, NSG America, and are sold under the trademark SELFOC®.

Endoscope designs can be quite complex in order to view and transmit the proper images from inside the body to the operator, as well as to attempt to compensate for chromatic aberrations and distortions. In addition to the lens components, a typical endoscope also uses a fiber bundle to transmit light from the ocular section to the area under observation. The fiber bundle is generally circular and surrounds the lenses interior to the endoscope's outer casing.

The use of fiber bundles for illumination in endoscopes suffers from a number of drawbacks. First, fiber bundles can be quite difficult to manufacture and add substantial cost to the overall endoscope. Second, fiber bundles transmit light to the end of the endoscope in the same circular configuration as it is put in, making for poor illumination of the image plane. Another major drawback with this form of endoscope is its inability to withstand the rigors of sterilization.

The use of an endoscope as a medical instrument requires sterilization between operations. Typically, hospitals employ the high temperature and pressure of an autoclave to sterilize medical instrumentation. Unfortunately, due to its size, the interior of the endoscope experiences very high temperatures during sterilization which can cause separation of the adhesive in the fiber optic bundle. Additionally, the cement holding connecting adjacent lenses can be compromised, allowing moisture to invade the lens and create fogging. Thus, although existing endoscopes function quite well, none is capable of repeatedly withstanding the demands of the sterilization process.

Accordingly, it is a primary object of the present invention to provide an endoscope with an improved ability to provide even illumination of an area under observation.

A further object of the present invention is to provide an endoscope that does not require the use of expensive and fragile fiber optic bundles to transmit light to the area under observation.

Yet another object of the present invention is to provide an endoscope that is relatively simple and inexpensive to manufacture.

An additional object of the present invention is to produce a reliable endoscope that may be manufactured so inexpensively that it is readily disposable.

These and other objects and advantages of the present invention will become apparent from consideration of the following description and drawings.

SUMMARY OF THE INVENTION

The present invention provides an endoscope with exceptional image transmission quality while being constructed inexpensively enough to be readily disposable.

The endoscope of the present invention comprises three basic parts-an ocular end, a relay section, and an objective end. Unlike existing endoscopes, the endoscope of one form of the present invention employs a series of relay lenses of differing diameters to provide both light and image transmission. A first relay lens (which may include a series of lenses) with a diameter larger than that of a second relay lens is connected to the objective end of the endoscope. The second relay lens is connected to the ocular end and is aligned in coaxial relation with the first relay lens. The endoscope is adapted to connect to a light source and transmit light from the light source down the excess diameter of the first relay lens to the area under observation, thereby eliminating the requirement of a fiber bundle or other means to transmit light to the objective end.

In another form of the endoscope of the present invention, the relay lens is surrounded by a light transmitting member, such as an acrylic or lucite tube surrounding the relay lens and terminating short of the ocular end of the relay lens through which light may be transmitted.

The endoscope of the present invention provides the exceptional image quality of a rigid endoscope while providing even better illumination of the examined area than is possible with existing endoscopes. Moreover, by eliminating the need for fiber optics, the cost of the entire unit is significantly reduced.

BRIEF DESCRIPTION OF THE DRAWINGS

The apparatus of the present invention should become apparent from the following description when considered in conjunction with the accompanying drawings, in which.

DETAILED DESCRIPTION OF THE INVENTION

The present invention provides an improved endoscope for use in all forms of applications, including medical and veterinary procedures. It can also be used in non-medical applications in hazardous areas that could destroy conventional endoscopes.

Figure 1:
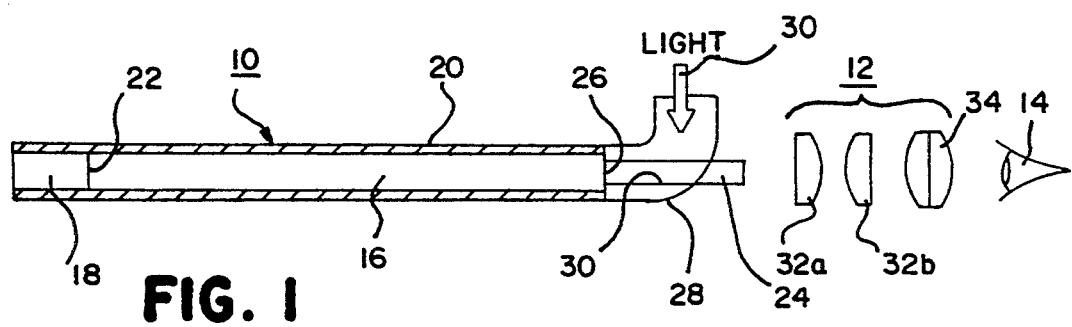
FIG. 1 is an exploded elevation view of one form of an endoscope of the present invention.

FIG. 1 depicts the basic component parts of an endoscope 10 of the present invention. The endoscope 10 includes an ocular section 12 interfacing with an operator's eye 14, a relay section 16 of one or more lenses, and an objective lens section 18 at the forward end thereof adapted to be inserted into a body to be examined.

The relay lens section 16 of the endoscope of the embodiment of FIG. 1 comprises a series of gradient-index rod lenses. Suitable relay lenses are commercially available from Nippon Sheet Glass under the trademark SELFOC ®. The relay and objective lenses are housed in a cylindrical casing 20 so that when they are inserted therein, they are oriented and maintained in coaxial relation. The casing 20 is preferably of stainless steel to provide strength and rigidity to the endoscope. Additionally, the outside surfaces of the rod lenses should be made non-reflecting by coating them with an optically black paint or similar material. It should be understood that multiple rod lenses may be arranged in series. In the illustration of FIG. 1, only a single rod lens is depicted.

Figure 2:
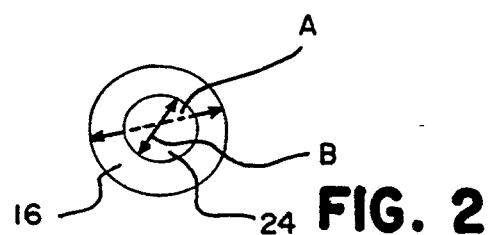
FIG. 2 is a plan view of the two tube sections of the present invention.

As shown, the gradient index rod lens 16 is joined in coaxial relation to objective lens 18 at the forward end of rod lens 16 with optical cement 22. A second gradient index rod lens 24 having a smaller diameter than lens 16 is joined to the opposite end of the rod lens 16 coaxially therewith by optical cement 26. FIG. 2 depicts the relation of lens 16 with diameter A to lens 24 with diameter B.

In order to illuminate the area under observation, a beam director 28, including a central opening 30, is mounted surrounding the lens 24 and directing light from a light source down that portion of lens 16 which is greater in diameter than lens 24. Although any light source may be employed, a halogen light source or a krypton light source is preferred. It is preferred that the beam director 28 comprise a single unit with an opening 30 formed therein to permit ease in mounting on lens 24 at the proper orientation.

The remainder of ocular section 12 serves to magnify the image for ease in viewing. In the embodiment illustrated in FIG. 1, the remainder of the ocular section 12 comprises two plano-convex lenses 32a, 32b and an achromatic lens 34.

In the preferred embodiment of the present invention, lens 16 is a gradient index rod lens with dimensions of 2.7 mm by 1.75 p (diameter×pitch) and lens 24 is a gradient index rod lens with dimensions of 2.0 mm by 0.25 p. It is necessary that the optical system of the relay lenses 16 and 24 have a total pitch equal to an integer (e.g. 1.75 p+0.25 p=2.0 p). The integer will be determined by the desired length of the endoscope and the selected diameters of lenses 16 and 24. Preferably, for best image translation, the ocular end relay lens 24 should be 0.25 pitch.

By way of example, an individual radial gradient-index rod lens may be provided in the form of a cylindrical rod that employs a parabolic index gradient, such as:

$$n(r)=n_o(1-Ar^2/2)$$

where r is the radial distance from the rod axis, n is the axial refractive index and A is a positive "gradient constant." Rays inside a radial gradient-index lens travel a sinusoidal path with a period of $2\pi/\sqrt{A}$. By changing the length L of the lens and the object distance from the lens, images of varying sizes and orientations may be produced.

Since GRIN endoscopes are susceptible to breakage and lens separation due to their long length and relatively small diameter, it is known that the stresses on the lens may be reduced by cutting a long relay lens into half period sections and introducing slight spaces between the sections. One such method is disclosed in U.S. Pat. No. 4,723,843 to Zobel.

The present invention may be practiced in conjunction with the relay lens optics similar to that disclosed in the '843 patent. Applying the present invention, the last lens in the relay lens series is removed and then replaced by a smaller diameter relay lens. This smaller diameter relay lens is surrounded by the beam director 28. Light from the light source 30 may then be reflected off of the beam director and down the excess diameter of the series of relay lenses.

The use of the relay lenses as described above permits the unit to be designed to be inexpensive enough to be disposable. In this manner, the ocular section may be reused while the relay lens section and the objective lens section may be discarded. Since a fiber bundle is no longer required to transmit light along the relay to the objective, these portions of the endoscope can now be manufactured quite easily and inexpensively.

Figure 3:
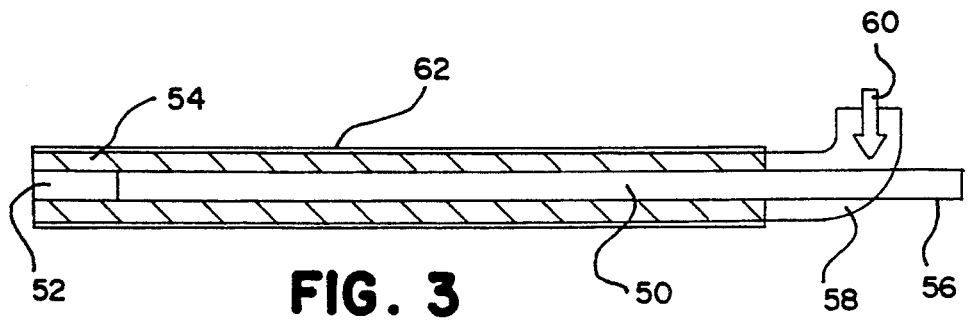
FIG. 3 is a longitudinal sectional view of a modified form of the present invention.
Figure 4:
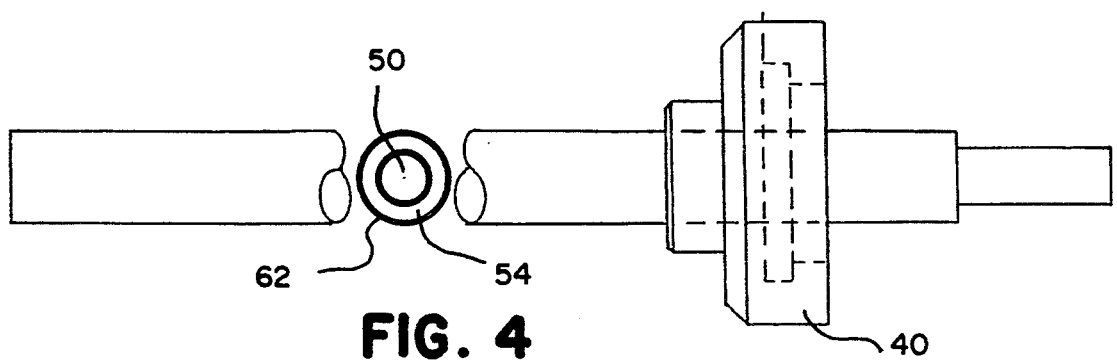
FIG. 4 is a side elevational view of the light and image end portion of an endoscope of the present invention with mounting means for securing the same to the occular end portion of the endoscope.

A modified form of the present invention is shown in FIG. 3 wherein a single reflex or rod lens 50 of uniform diameter is provided. This lens 50 may be of single or multiple sections. An objective lens 52 is secured by optical cement to the forward end of the reflex lens 50. Surrounding the reflex lens 50 and objective lens 52 is a light transmitting tube 54 of acrylic or similar material. This light transmitting tube terminates short of the ocular end 56 of the reflex lens 50. A beam director 58 and a suitable light source 60 are provided to transmit light to and through the tube 54. Also, a casing 62 of stainless steel or other material surrounds the tube 54 and reflex lens and objective lens to protect and support the same during use. The outer casing 62 may have a mounting bracket such as one half of a Luer fitting to permit attachment to an ocular lens section.

Figure 5:
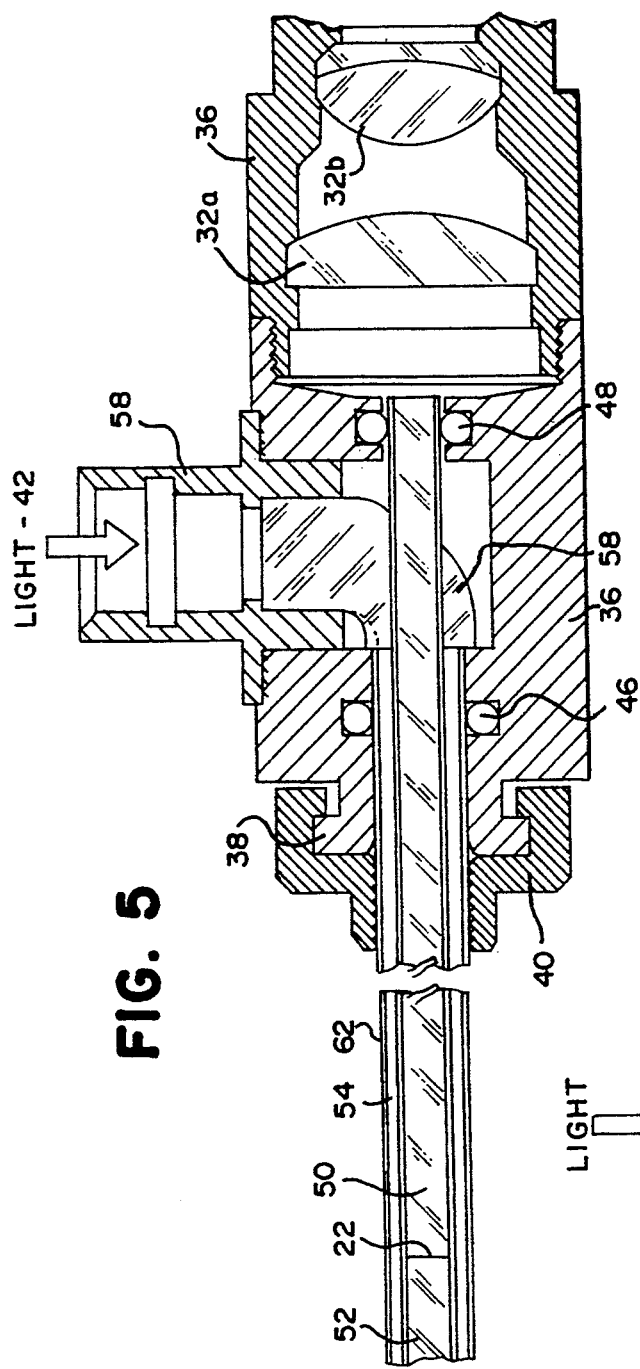
FIG. 5 is a longitudinal sectional view of the complete assembled endoscope of the present invention.
Figure 6:
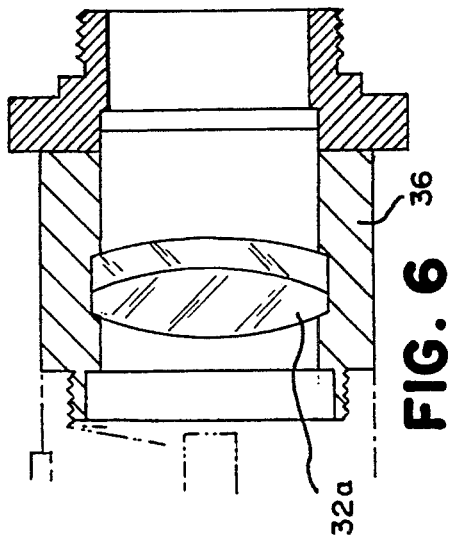
FIG. 6 is a longitudinal sectional view of a camera adapter for the endoscope.
Figure 7:
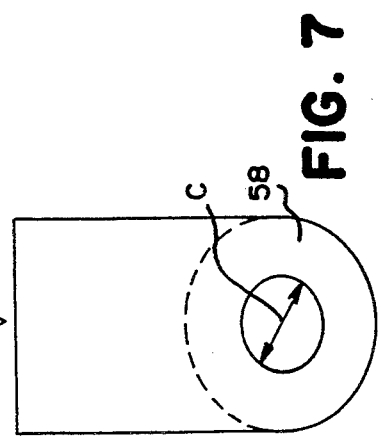
FIG. 7 is a face view of one form of beam director for transmitting light to the endoscope lens.

FIG. 5 illustrates the details of one embodiment of the ocular section 36 of an endoscope of the present invention. In this embodiment, the ocular lens housing 36 is releasably attached to relay lens section 16. The relay lens 16 and the objective lens (not shown) which is an integral part of the relay lens are disposable, thus eliminating the requirement that they are able to withstand the negative effects encountered in the medical sterilization process.

In contrast, the ocular section housing 36 is formed of stainless steel or similar material which may be sterilized and reused repeatedly. To avoid damage to the lenses in the housing 36 during sterilization, the lenses can be releasably mounted within the housing section 36.

The ocular lens section 36 houses the gradient index rod lens 50 and light transmitter tube 54, which terminates short of the first plano-convex lens 32a. As has been described, the diameter of rod lens 50 is less than the diameter of the aligned light transmitting tube 54. The disposable relay and objective lens section can be removably secured to the ocular lens housing, for example, by means of a luer fitting 38 including a collar 40 carried by the outer casing 62 for the relay and objective lenses. In a similar manner, the relay lens system of FIG. 1 can also be used with the occular lens section 36.

Light supply is provided by light source means 42. In this embodiment, light travels from light source 42 into housing 36 via beam director 58.

An O-ring 46 is mounted in the relay lens end of the housing to engage and seal with the relay lens assembly. Similarly, a second O-ring 48 is provided at the end of the lens 50 to seal with the housing 36.

The apparatus of the various embodiments of the present invention provide a superior endoscopic image with better object illumination than is possible with existing endoscopes due to the absence of multiple glass/air interfaces. Moreover, by replacing fiber optics as the light transition means, the apparatus of the present invention can be produced at a fraction of the cost of existing systems. One of the many benefits of the cost savings is that the present invention can be produced inexpensively so that it can be disposable.

While particular embodiments of the present invention have been illustrated and described herein, the present invention should not be limited to such illustrations and description. It should be apparent that changes and modifications may be incorporated and embodied as part of the present invention within the scope of the following claims.

What is claimed is:

1. An endoscope for viewing an area having an ocular end, a relay lens section, an objective lens end and a light transmitting section, comprising;
   a first lens system including the relay lens section and an objective lens section, the objective lens section terminating at the area to be viewed;
   said light transmitting section surrounding said objective lens section and a portion of said relay lens section adjacent said objective lens section terminating short of said ocular end;
   light means for illuminating said area to be viewed for transmitting light waves down said light transmitting section; and
   means for removably securing said first lens system and said light transmitting section to said ocular end.

2. The endoscope in accordance with claim 1 wherein said light means includes a beam director surrounding the relay lens section beyond the termination of said light transmitting section at the ocular end of said endoscope, and a source of light directed toward said beam direction and reflected therefrom toward said light transmitting section.

3. The endoscope of claim 2 wherein said light transmitting section comprises a cylindrical tube of acrylic material closely surrounding said objective lens section and said portion of said relay lens section.

4. The endoscope of claim 3 including a supporting tube surrounding said light transmitting section, and said means for removably securing said first lens system to said ocular end engaging said supporting tube.

5. An endoscope for viewing an area comprising:
   (a) a relay lens section having a first end, a second end, a light transmitting portion, and an image transmitting portion;
   (b) an objective lens section having a first end and a second end, the first end attached to the first end of the relay lens section, the second end terminating at the area to be viewed; and
   (c) an ocular section removably secured to the second end of the relay lens section so that images received through the image transmitting portion of the relay lens section may be viewed.

6. The endoscope of claim 5 having light means including a light source and a beam director, said beam director surrounding the image transmitting portion of the relay lens section and directing light down the light transmitting portion of the relay lens section to the objective lens section.

7. The endoscope of claim 6 wherein the light transmitting portion of the relay lens section comprises a cylindrical tube of acrylic material closely surrounding the image transmitting portion of the relay lens section.

8. The endoscope of claim 6 wherein the light transmitting portion of the relay lens section comprises the outer periphery of the relay lens section.

9. The endoscope of claim 6 wherein the relay lens section is insertable into the ocular section and removably attachable to the ocular section.

10. The endoscope of claim 9 wherein the ocular section houses the beam director.

* * * * *